United States Patent [19]

van Andel

[11] Patent Number: Plant 5,507

[45] Date of Patent: Jul. 2, 1985

[54] CARNATION NAMED STANBRODA

[75] Inventor: Jacob van Andel, Aalsmeer, Netherlands

[73] Assignee: B. V. Handelskwekerij, M. C. van Staaveren, Aalsmeer, Netherlands

[21] Appl. No.: 556,681

[22] Filed: Nov. 30, 1983

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new red carnation variety characterized by its deep red coloration, large size and many closely-spaced petals of uniform color, by its continuous blooming and strong upright growth habit with abundant production of foliage and strong resistance to fusarium oxysporum.

1 Drawing Figure

BACKGROUND OF THE NEW PLANT

This new carnation plant was discovered by me as a sport of the carnation variety "Londorga" (unpatented) growing among a stand of carnation plants maintained in greenhouse at Aalsmeer, Holland, for breeding purposes. The large size and solid red coloring of the relatively large number of petals made me realize that I had found a carnation having excellent possibilities for the cut flower market and I promptly began propagation of the plant by means of cuttings from the discovery variety at Aalsmeer to test its growth characteristics, as well as its retention of bloom and color characteristics. Continued propagation of this new plant, through several successive generations at Aalsmeer, has demonstrated that the new plant has very excellent growth habits and retains its novel characteristics from generation to generation so that they appear to be firmly fixed.

DESCRIPTION OF THE DRAWING

My new variety of carnation plant is illustrated by the accompanying photographic drawing which shows, in full color, a three-quarter face view of a fully opened flower, the colors shown being as nearly true as it is reasonably possible to obtain by conventional photographic procedures.

DESCRIPTION OF THE NEW PLANT

The following is a detailed description of my new carnation plant based upon observations of greenhouse grown plants made at Aalsmeer, Holland, in the summer of 1983, the color designations being according to The R.H.S. Colour Chart of The Royal Horticultural Society at London, England.

THE PLANT

Origin: Sport.

Parentage: Carnation variety "Londorga", the parentage of which is unknown.

Classification:

*Botanic.*—Hybrid *Dianthus caryophyllus.*

*Commercial.*—Carnation.

Form: Leafy bush.

Height: Average tall.

Growth: Upright and of good strength.

Branching: Normal and upright.

Foliage:

*Quantity.*—Abundant.

*Number of leaves.*—Depends upon the season.

*Size of leaf.*—Medium and of oblong shape.

*Texture.*—Smooth.

*Color.*—Upper side and under side — Blue/Green with waxy layer.

THE BUD

Size: Medium.

*Diameter.*—About 1.5 cm.

*Length.*—About 3 cm.

Shape: Cylindrical.

Color of petals: When sepals first divide and petals begin to unfurl — 46A.

Sepals:

*Number.*—Five.

*Color.*—Both inside and outside — Grey/Green.

Calyx:

*Size.*—Large.

*Aspect.*—Smooth.

*Splitting.*—Hardly ever.

THE FLOWER

Blooming habit: Continuous.

Size: Large.

*Average diameter.*—About 8 cm.

*Average depth.*—About 4 cm.

Borne: Singly, after disbudding.

Opening: Regular.

Petalage:

*Number of petals.*—Approximately 50 to 60.

*Arrangement.*—More-or-less imbricated.

*Form.*—Fan shaped with generally entire margins.

*Texture.*—Soft.

*Appearance.*—Satiny.

*Color.*—All petals and for all seasons: Upper side — R.H.S. 47A. Under side — R.H.S. 47A.

Peduncle or flower stem:

*Length.*—Depends upon season.

*Character.*—Strong and upright.

*Color.*—Dark green.

Persistence: Petals hang on and dry.

Fragrance: Lightly fragrant.

Disease resistance: Appears to be less susceptible to fusarium oxysporum as observed at Aalsmeer, Holland.

Lasting quality:

*On plant.*—20 Days.

*As cut flower.*—10 To 15 days.

REPRODUCTIVE ORGANS

Stamens:

*Number.*—Medium.

*Anthers.*—Of medium size and of cream color with pink at top.

*Pollen.*—None.

Pistils:

*Number.*—One.

*Style.*—Length: About 30 mm. Color: White/-Cream.

This new carnation variety most resembles the variety "Londorga" (unpatented). However, the very deep and solid red coloration of the bloom is quite new and because of its size and its many petals, the flower has a very distinctive and novel appearance.

I claim:

1. The new and distinct variety of carnation plant, substantially as herein shown and described, characterized by its continuous year round production of relatively large blossoms, and the stability of the flower color which holds through all seasons.

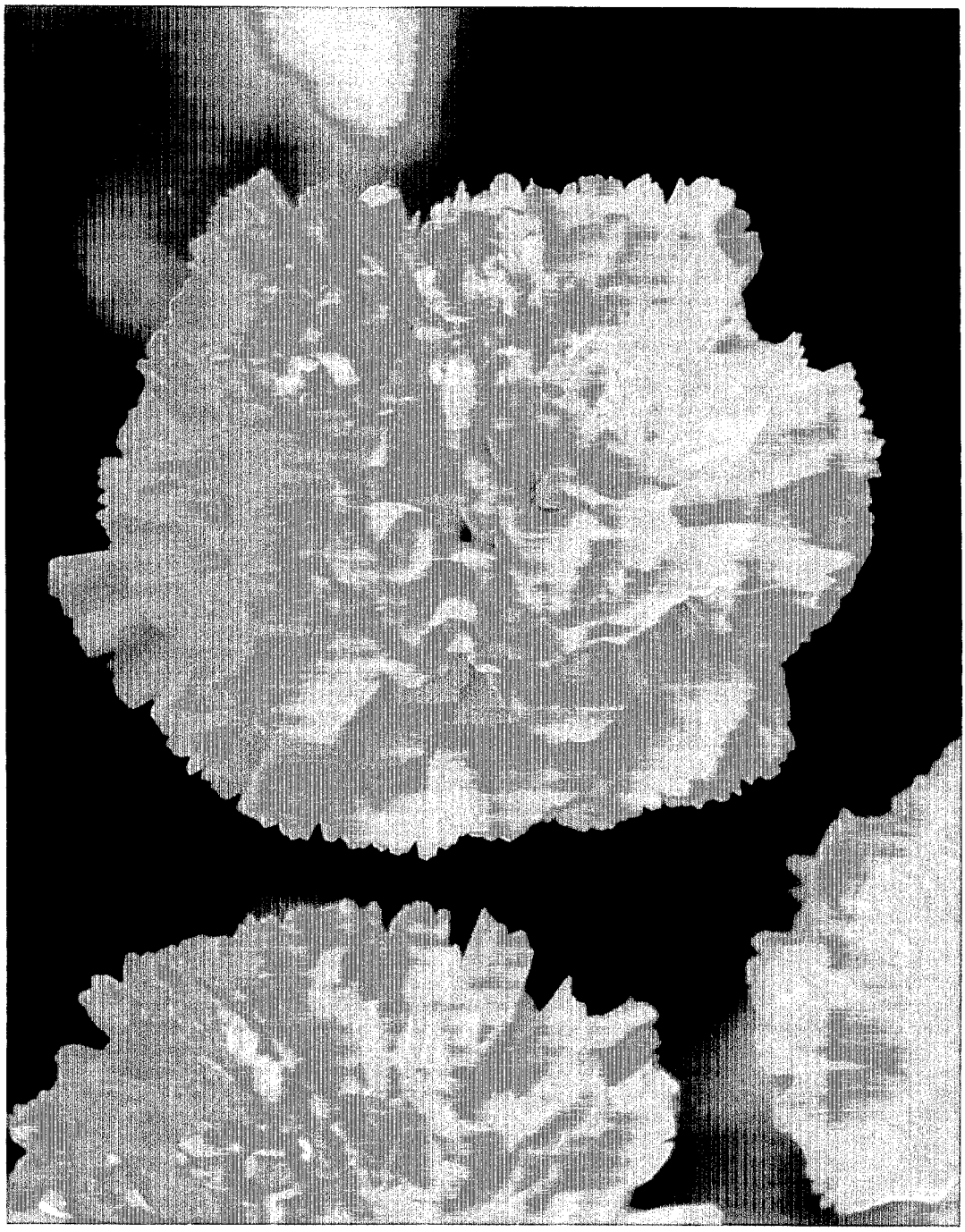

* * * * *